(12) United States Patent
Toda

(10) Patent No.: US 6,393,920 B1
(45) Date of Patent: May 28, 2002

(54) SOUND PRESSURE SENSING DEVICE

(76) Inventor: Kohji Toda, 1-49-18 Futaba, Yokosuka 239-0814 (JP)

( * ) Notice: Subject to any disclaimer, the term of this patent is extended or adjusted under 35 U.S.C. 154(b) by 0 days.

(21) Appl. No.: 09/557,057

(22) Filed: Apr. 21, 2000

(51) Int. Cl.$^7$ .............................. G01L 9/06; H01L 41/04
(52) U.S. Cl. ........................ 73/721; 73/727; 310/334; 310/324; 600/485
(58) Field of Search ......................... 73/721, 727, 702, 73/703, 715, 704; 600/485, 500, 561, 586; 310/311, 313 R, 313 A, 313 B, 334, 322, 324

(56) References Cited

U.S. PATENT DOCUMENTS

| | | | | |
|---|---|---|---|---|
| 3,745,812 A | * | 7/1973 | Korpel | 73/67.5 R |
| 4,775,961 A | * | 10/1988 | Copek et al. | 367/140 |
| 5,006,749 A | * | 4/1991 | White | 310/323 |
| 5,129,262 A | * | 7/1992 | White et al. | 73/599 |
| 5,532,538 A | * | 7/1996 | Jin et al. | 310/313 R |
| 5,798,597 A | * | 8/1998 | Toda | 310/313 R |
| 6,060,812 A | * | 5/2000 | Toda | 310/313 R |

\* cited by examiner

Primary Examiner—Benjamin R. Fuller
Assistant Examiner—Abdullahi Aw-Musse

(57) ABSTRACT

A sound pressure sensing device comprises a piezoelectric substrate, an input interdigital transducer, a first output interdigital transducer, a second output interdigital transducer, a diaphragm, a liquid tank, and a signal analyzer. All the input-, the first output-, and the second output interdigital transducers are formed on one end surface of the piezoelectric substrate. The liquid tank has a liquid in contact with the other end surface of the piezoelectric substrate and an inner surface of the diaphragm. If an input electric signal is applied to the input interdigital transducer, an elastic wave is excited in the piezoelectric substrate. A leaky component of the elastic wave is radiated effectively in the form of a longitudinal wave into the liquid. The longitudinal wave is reflected in the liquid by the diaphragm. A reflected longitudinal wave is detected at the first output interdigital transducer as a first delayed electric signal. A non-leaky component of the elastic wave is detected at the second output interdigital transducer as a second delayed electric signal. A sound pressure caused by touching an outer surface of the diaphragm is sensed by the signal analyzer from a difference between the first- and second delayed electric signals.

19 Claims, 9 Drawing Sheets

SOUND PRESSURE SENSING DEVICE

BACKGROUND OF THE INVENTION

1. Field of the Invention

The present invention relates to a device for sensing a sound pressure by means of using a sensing assembly composed of a piezoelectric substrate, an input interdigital transducer, a first- and a second output interdigital transducers.

2. Description of the Prior Art

There are two types, that is, a touch-type and an untouch-type, of conventional devices for sensing a sound pressure. For example, an electric micrometer for measuring a minute displacement, a linear scale for a large displacement, and a rotary encoder for a rotation displacement belong to the touch-type of device. The electric micrometer and the linear scale is used as, for example, a reference for measuring the length of a material. The rotary encoder is used for controlling a rotation velocity or a rotation frequency of a rotatory material. The touch-type of device has some problems on measurement accuracy, response time, difficulty in use, durability and manufacturing. On the other hand, for example, a laser-type sensor and an electroacoustic-type sensor belong to the untouch-type of device. The laser-type sensor including a semiconductor position-sensing device is mainly used for measuring a vibration displacement along the direction vertical to the laser beam applied to a material. The laser-type sensor has a defect that the longer the length of the laser beam, the lower the measurement accuracy because of flickering of the laser beam itself. In addition, the use of the laser-type sensor is impossible for the measurement in opaque media. The electroacoustic-type sensor is used for measuring the vibration displacement in a material near a terminal of a pipe. The electroacoustic-type sensor is easy to be affected by a change in circumstances, and has some problems on measurement accuracy, and so on.

SUMMARY OF THE INVENTION

An object of the present invention is to provide a sound pressure sensing device capable of sensing a sound pressure caused by touching a diaphragm constructed on the device with a high sensitivity.

Another object of the present invention is to provide a sound pressure sensing device capable of operating at a high frequency.

Another object of the present invention is to provide a sound pressure sensing device capable of transducing a sound pressure to an electric signal.

Another object of the present invention is to provide a sound pressure sensing device excellent in measurement accuracy, response time, durability, manufacturing.

Another object of the present invention is to provide a sound pressure sensing device which is not affected by a change in circumstances, for example, a change in temperature.

A still other object of the present invention is to provide a sound pressure sensing device easy in use and having a small size which is very light in weight and has a simple structure.

According to one aspect of the present invention there is provided a sound pressure sensing device comprising a piezoelectric substrate having two end surfaces, an input interdigital transducer, a first output interdigital transducer, a second output interdigital transducer, a diaphragm having an inner- and an outer surfaces, a liquid tank, and a signal analyzer. All the input-, the first output-, and the second output interdigital transducers are formed on one end surface of the piezoelectric substrate. The liquid tank has a liquid in contact with the other end surface of the piezoelectric substrate and the inner surface of the diaphragm.

If an input electric signal is applied to the input interdigital transducer, an elastic wave is excited in the piezoelectric substrate. A leaky component of the elastic wave is radiated effectively in the form of a longitudinal wave into the liquid. The longitudinal wave is reflected in the liquid by the diaphragm. A reflected longitudinal wave is detected at the first output interdigital transducer as a first delayed electric signal. A non-leaky component of the elastic wave is detected at the second output interdigital transducer as a second delayed electric signal. A sound pressure caused by touching the outer surface of the diaphragm is sensed by the signal analyzer from a difference between the first- and second delayed electric signals.

According to another aspect of the present invention there is provided an amplifier connected between the input interdigital transducer and the second output interdigital transducer. A part of the second delayed electric signal is amplified via the amplifier, and is fed back as the input electric signal again. Thus, the input interdigital transducer, the second output interdigital transducer and the amplifier form a self-oscillation type of delay-line oscillator.

According to another aspect of the present invention there is provided an amplifier connected between the input interdigital transducer and the first output interdigital transducer. A part of the first delayed electric signal is amplified via the amplifier, and is fed back as the input electric signal again. Thus, the input interdigital transducer, the first output interdigital transducer and the amplifier form a self-oscillation type of delay-line oscillator.

According to another aspect of the present invention there is provided a signal analyzer comprising a phase comparator, which compares an acoustic phase delay of the first delayed electric signal with that of the second delayed electric signal. Thus, a sound pressure is sensed in terms of a phase difference between the first- and second delayed electric signals.

According to another aspect of the present invention there are provided an input-, a first output-, and a second output interdigital transducers having an arch-shape, respectively, and arranged to have one concentric center.

According to another aspect of the present invention there is provided a piezoelectric substrate made of a piezoelectric ceramic thin plate, of which the polarization axis is parallel to the thickness direction thereof According to another aspect of the present invention there is provided a piezoelectric polymer thin plate.

According to another aspect of the present invention there is provided a diaphragm made of a polymer film.

According to other aspect of the present invention there is provided a diaphragm made of a metal film.

According to a further aspect of the present invention there is provided a sound pressure sensing device comprising a piezoelectric substrate having two end surfaces, an input interdigital transducer, a first output interdigital transducer, a second output interdigital transducer, a tank, and a signal analyzer. All the input-, the first output-, and the second output interdigital transducers are formed on one end surface of the piezoelectric substrate. The tank has a liquid room with a liquid in contact with the other end surface of the piezoelectric substrate, an air room with a diaphragm panel having an inner- and an outer surfaces, and a partition wall between the liquid- and air rooms.

If an input electric signal is applied to the input interdigital transducer, an elastic wave is excited in the piezoelectric substrate. A leaky component of the elastic wave is radiated effectively in the form of a longitudinal wave into the liquid. The longitudinal wave is reflected in the liquid by the partition wall. A reflected longitudinal wave is detected at the first output interdigital transducer as a first delayed electric signal. A non-leaky component of the elastic wave is detected at the second output interdigital transducer as a second delayed electric signal. A sound pressure caused by touching the outer surface of the diaphragm panel is sensed by the signal analyzer from a difference between the first- and second delayed electric signals.

BRIEF DESCRIPTION OF THE DRAWINGS

Other features and advantages of the invention will be clarified from the following description with reference to the attached drawings.

DETAILED DESCRIPTION OF THE PRESENTLY PREFERRED EXEMPLARY EMBODIMENTS

Figure 1:
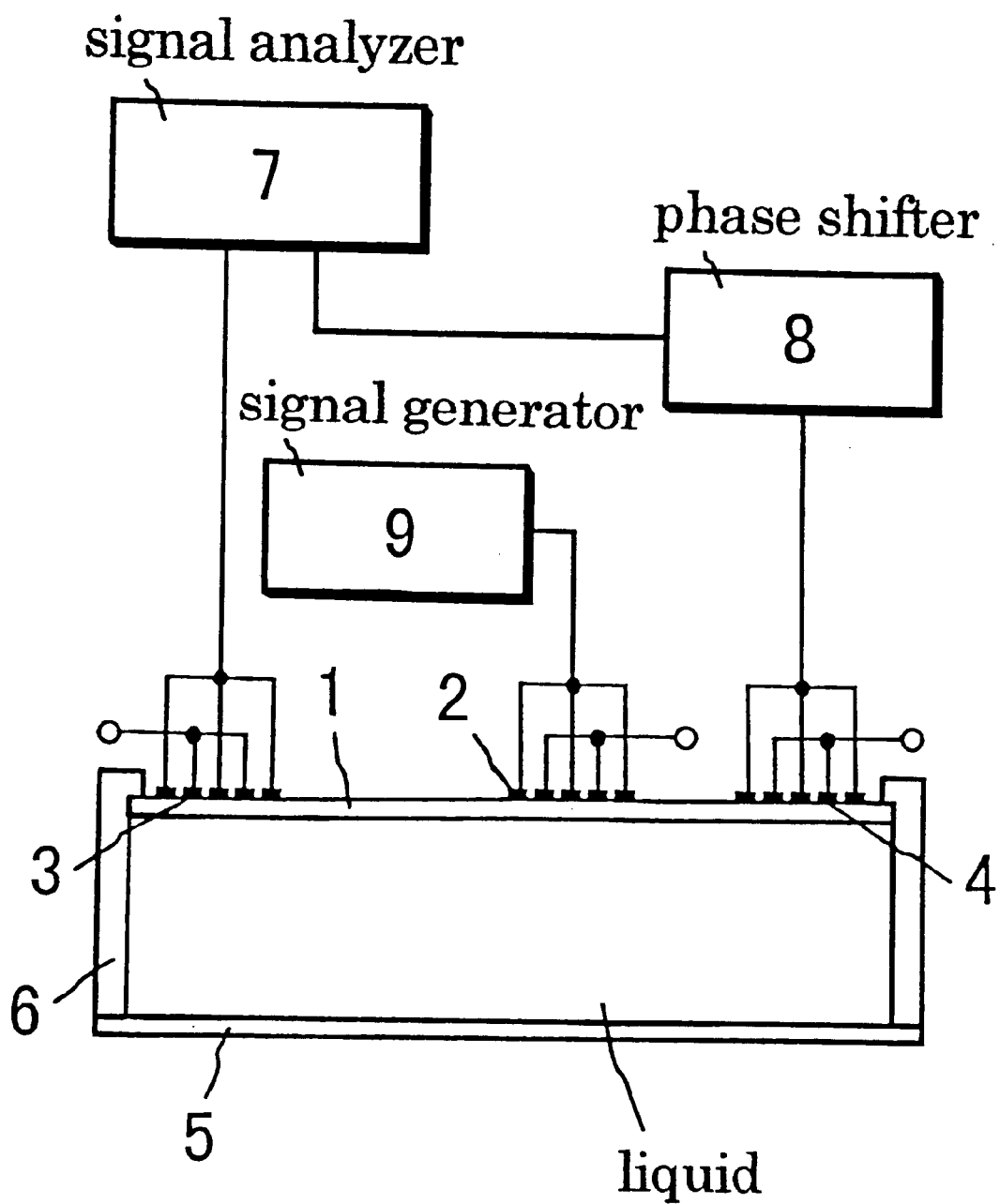
FIG. 1 shows a schematic illustration of a sound pressure sensing device according to a first embodiment of the present invention.

FIG. 1 shows a schematic illustration of a sound pressure sensing device according to a first embodiment of the present invention. The sound pressure sensing device comprises piezoelectric substrate 1, input interdigital transducer 2, first output interdigital transducer 3, second output interdigital transducer 4, diaphragm 5, liquid tank 6, signal analyzer 7, phase shifter 8, and signal generator 9. Piezoelectric substrate 1 is made of a piezoelectric ceramic thin plate. It is possible to use a piezoelectric polymer plate as piezoelectric substrate 1. Input interdigital transducer 2, first output interdigital transducer 3 and second output interdigital transducer 4, having an arch-shape and made of an aluminum thin film, respectively, are formed on one end surface of piezoelectric substrate 1. Diaphragm 5 is made of a phosphor bronze, a polymer film, or a rubber film. A liquid in liquid tank 6 is in contact with the other end surface of piezoelectric substrate 1 and an inner surface of diaphragm 5. Piezoelectric substrate 1, input interdigital transducer 2, first output interdigital transducer 3 and second output interdigital transducer 4 form a sensing assembly. Signal analyzer 7 is made of a phase comparator. When sensing, for example, a person's pulse, that is a sound pressure generated by a blood vessel vibration, an outer surface of diaphragm 5 is kept in touching with, for example, a human wrist. Thus, the sound pressure sensing device in FIG. 1 has a small size which is very light in weight and has a simple structure.

Figure 2:
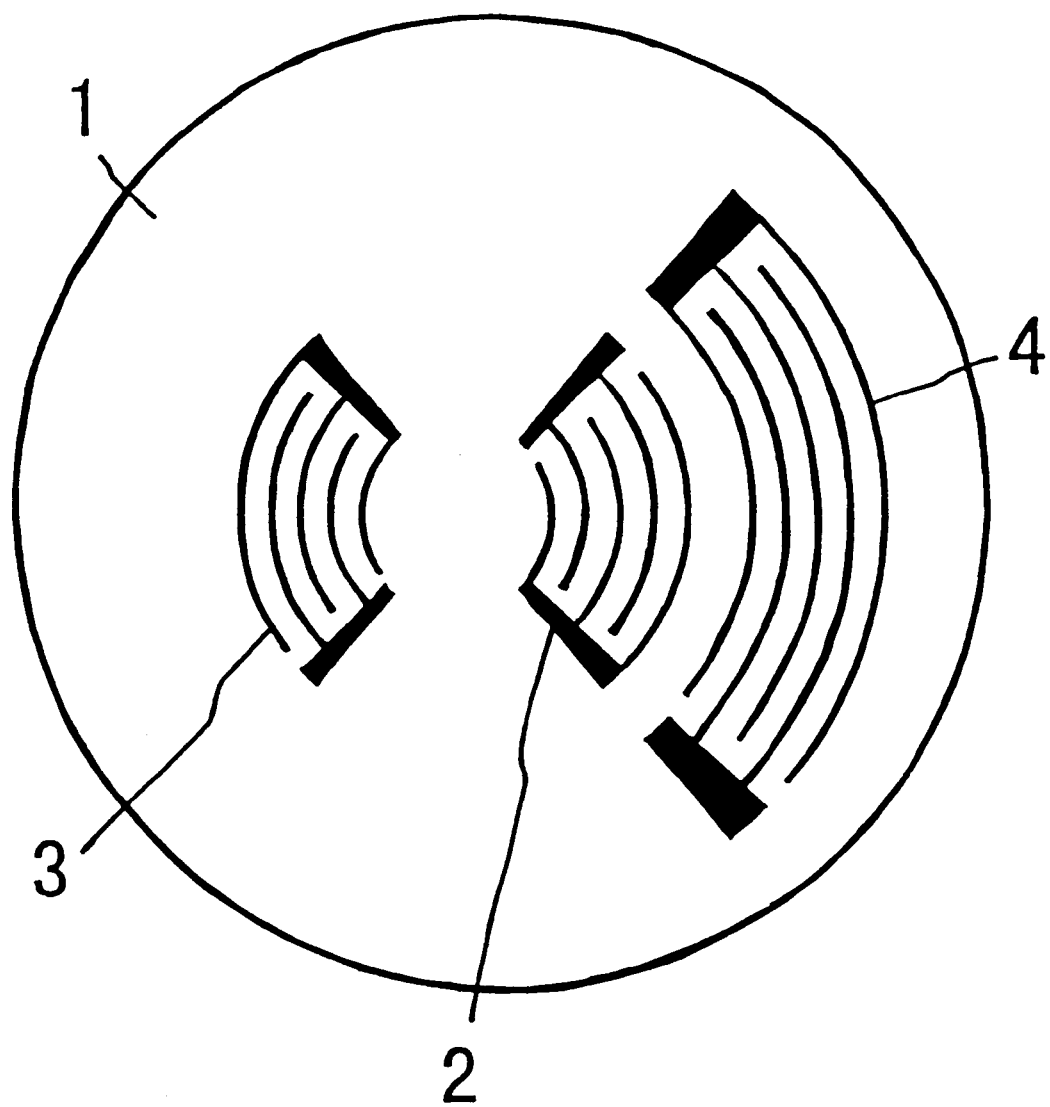
FIG. 2 shows a top plan view of the sensing assembly shown in FIG. 1.
Figure 3:
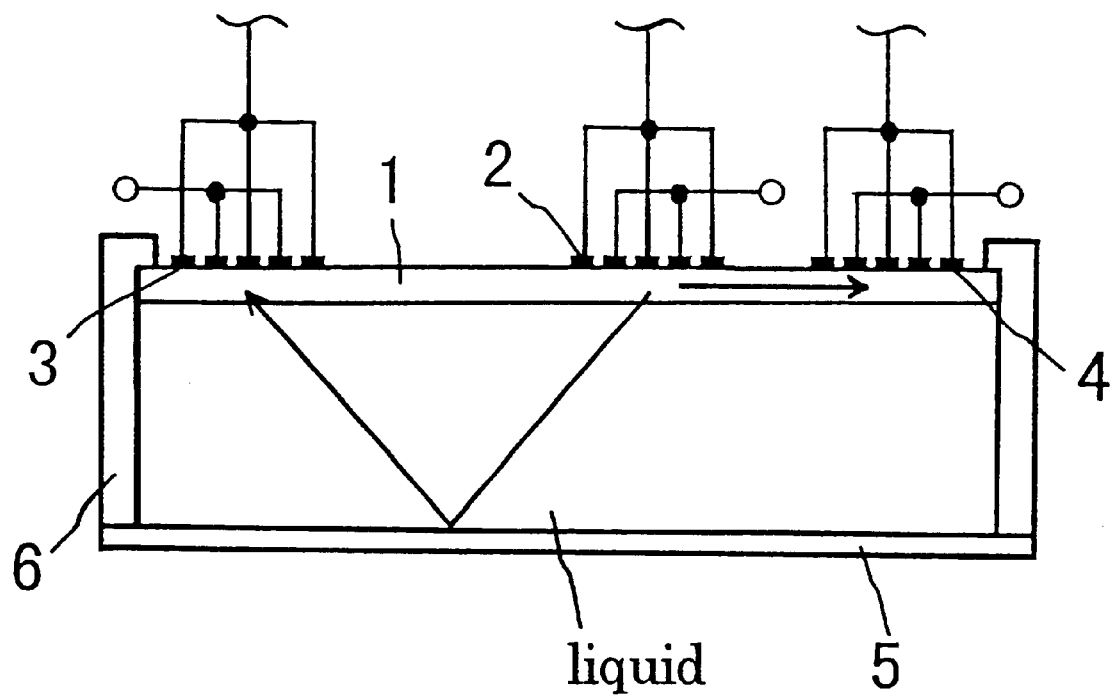
FIG. 3 shows an illustration exhibiting a path of the longitudinal wave traveling in the liquid by an arrow.

FIG. 2 shows a top plan view of the sensing assembly shown in FIG. 1. The separation length between input interdigital transducer 2 and first output interdigital transducer 3 is 6 mm. Input interdigital transducer 2, first output interdigital transducer 3 and second output interdigital transducer 4 are arranged to have one concentric center, and have an aperture angle of 45°, an interdigital periodicity of 340 μm and 5 finger pairs, respectively. When sensing a person's pulse, the outer surface of diaphragm 5 is put on a skin near a blood vessel.

In the sound pressure sensing device in FIG. 1, if an input electric signal, with a frequency approximately corresponding to an interdigital periodicity of input interdigital transducer 2, is applied from signal generator 9 to input interdigital transducer 2, an elastic wave is excited in piezoelectric substrate 1. Because piezoelectric substrate 1 is made of a piezoelectric ceramic, and in addition, the polarization axis thereof is parallel to the thickness direction thereof, the elastic wave is excited in piezoelectric substrate I effectively. A leaky component of the elastic wave having the wavelength approximately equivalent to the interdigital periodicity is radiated effectively in the form of a longitudinal wave into the liquid, in other words, a mode conversion from the leaky component of the elastic wave to the longitudinal wave in the liquid occurs. Such effective radiation is owing to the arch-shape of input interdigital transducer 2, which enables an ultrasound beam to go along a slant direction to the other end surface of piezoelectric substrate 1. The longitudinal wave is reflected in the liquid by diaphragm 5. A reflected longitudinal wave is detected at first output interdigital transducer 3 as a first delayed electric signal with a frequency approximately corresponding to the interdigital periodicity. Such detection of the first delayed electric signal is due to the arch-shape of first output interdigital transducer 3, which can detect an ultrasound beam from a slant direction to the inner surface of diaphragm 5. On the other hand, a non-leaky component of the elastic wave is transmitted to second output interdigital transducer 4, and detected at second output interdigital transducer 4 as a second delayed electric signal. Then, an acoustic phase delay of the first delayed electric signal is compared with that of the second delayed electric signal at signal analyzer 7. In this time, the phase of the first delayed electric signal is controlled to be coincident with that of the second delayed electric signal by phase shifter 8, when sensing no sound pressure.

Figure 8:
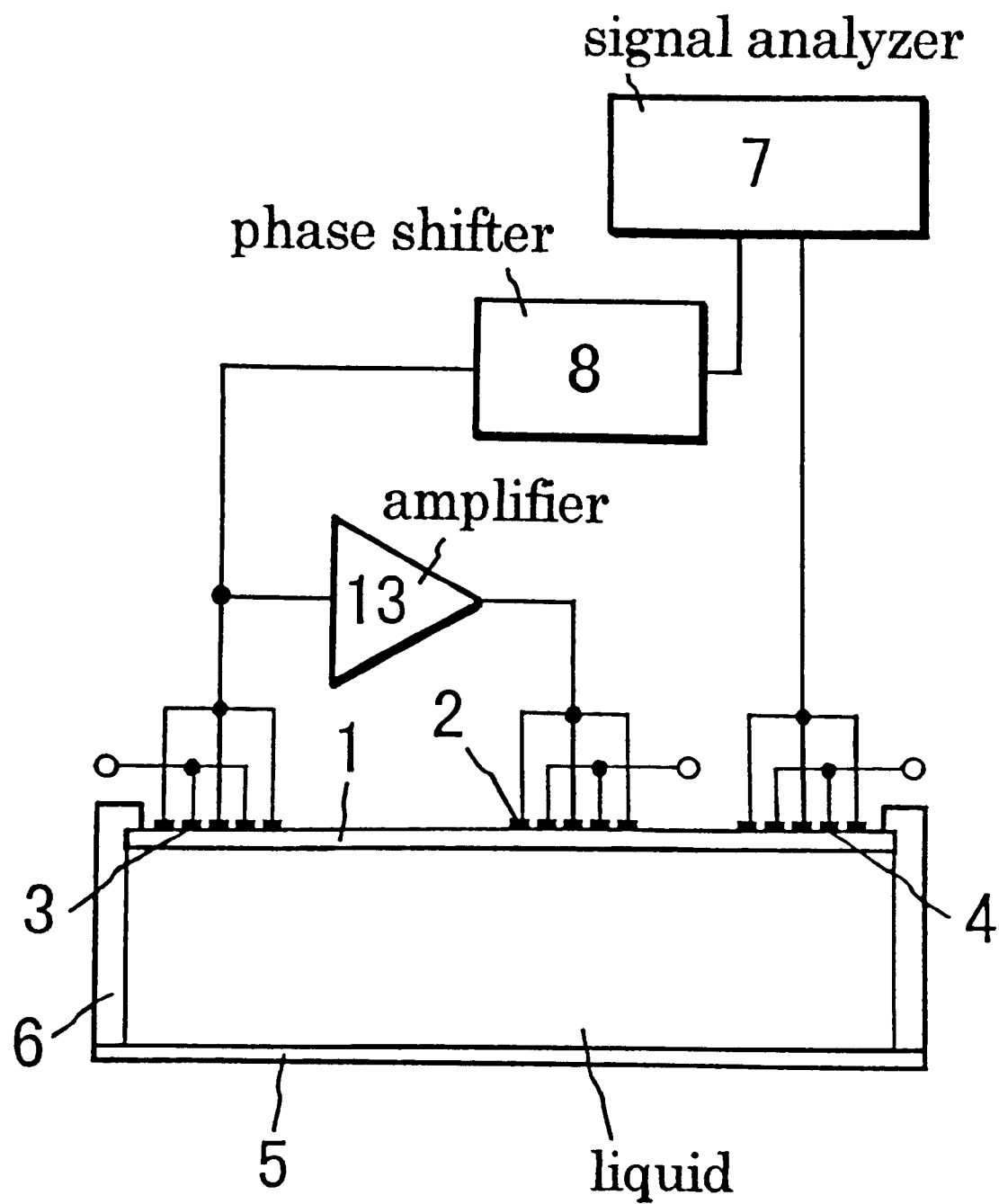
FIG. 8 shows a schematic illustration of a sound pressure sensing device according to a third embodiment of the present invention.

FIG. 8 shows an illustration exhibiting a path of the longitudinal wave traveling in the liquid by an arrow. If diaphragm 5 senses a sound pressure, diaphragm 5 is mechanically vibrated. As a result, a length of traveling path of the longitudinal wave is changed. A change in length of traveling path brings about a difference between an acoustic phase delay of the first delayed electric signal and that of the second delayed electric signal. Accordingly, a sound pressure through diaphragm 5 can be sensed by signal analyzer 7 in terms of a phase difference. In addition, such a sensing system as comparing the two phases is not affected by a temperature change. Thus, it is possible to measure, for example, a person's pulse a minute with a high sensitivity.

Figure 4:
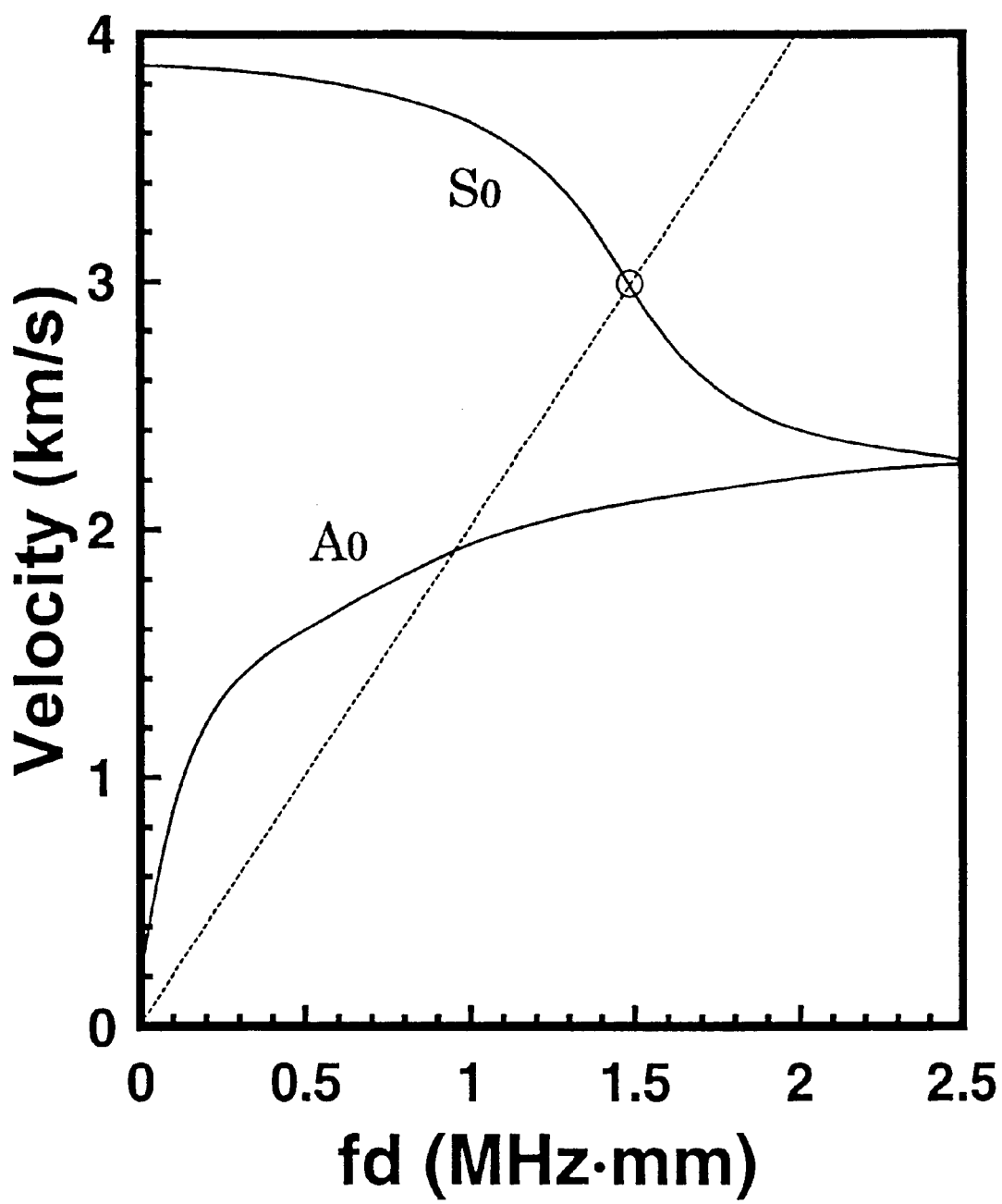
FIG. 4 shows a relationship between the phase velocity of an elastic wave for the $A_0$ mode an d the $S_0$ mode in piezoelectric substrate 1, and the product fd.

FIG. 4 shows a relationship between the phase velocity of an elastic wave for the $A_0$ mode and the $S_0$ mode in piezoelectric substrate 1, and the product fd, where f is a frequency of the elastic wave and d is a thickness of piezoelectric substrate 1. Piezoelectric substrate 1 has a shear wave velocity of 2,460 m/s and a longitudinal wave velocity of 4,390 m/s.

Figure 5:
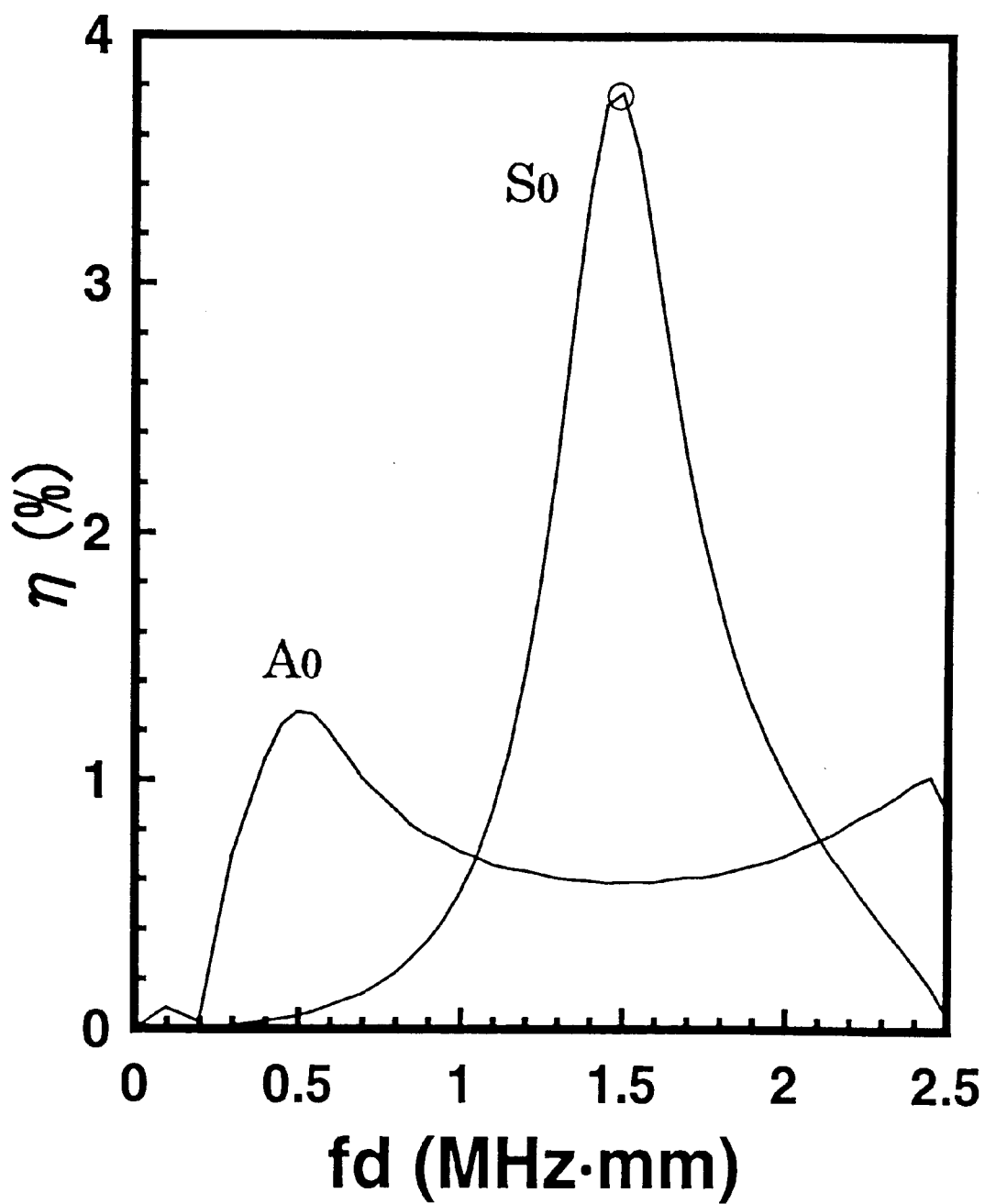
FIG. 5 shows a relationship between the calculated transducer efficiency η for a longitudinal wave radiation into water, and the product fd.

FIG. 5 shows a relationship between the calculated transducer efficiency η for a longitudinal wave radiation into water, and the product fd. It should be noted that the $S_0$ mode curve has the highest peak at around 1.5 MHz·mm, that is the most appropriate operation condition.

Figure 6:
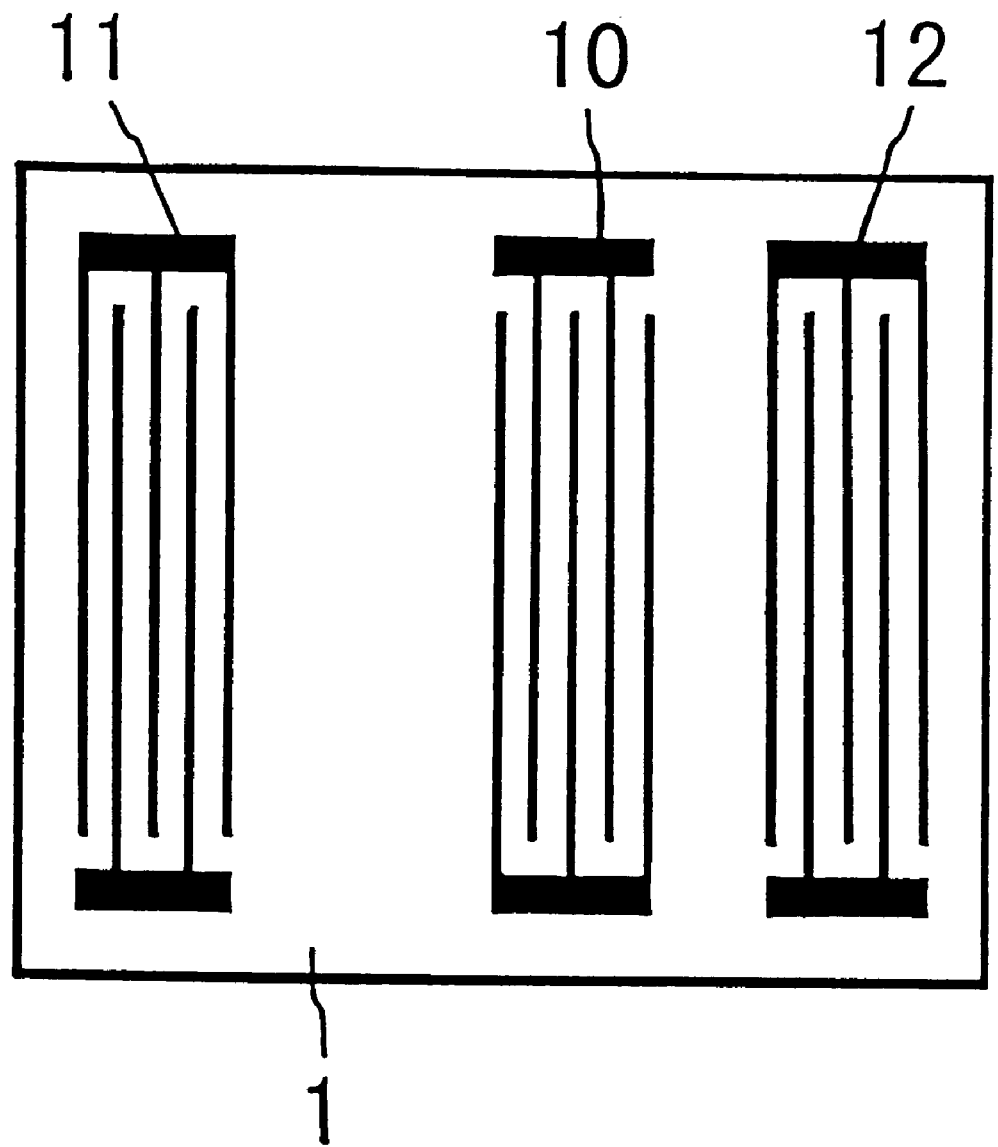
FIG. 6 shows a top plan view of another sensing assembly used in place of the assembly in FIG. 2.

FIG. 6 shows a top plan view of another sensing assembly used in place of the assembly in FIG. 2. The sensing assembly in FIG. 6 comprises piezoelectric substrate 1, input interdigital transducer 10, first output interdigital transducer 11 and second output interdigital transducer 12, and has the same function as FIG. 2.

Figure 7:
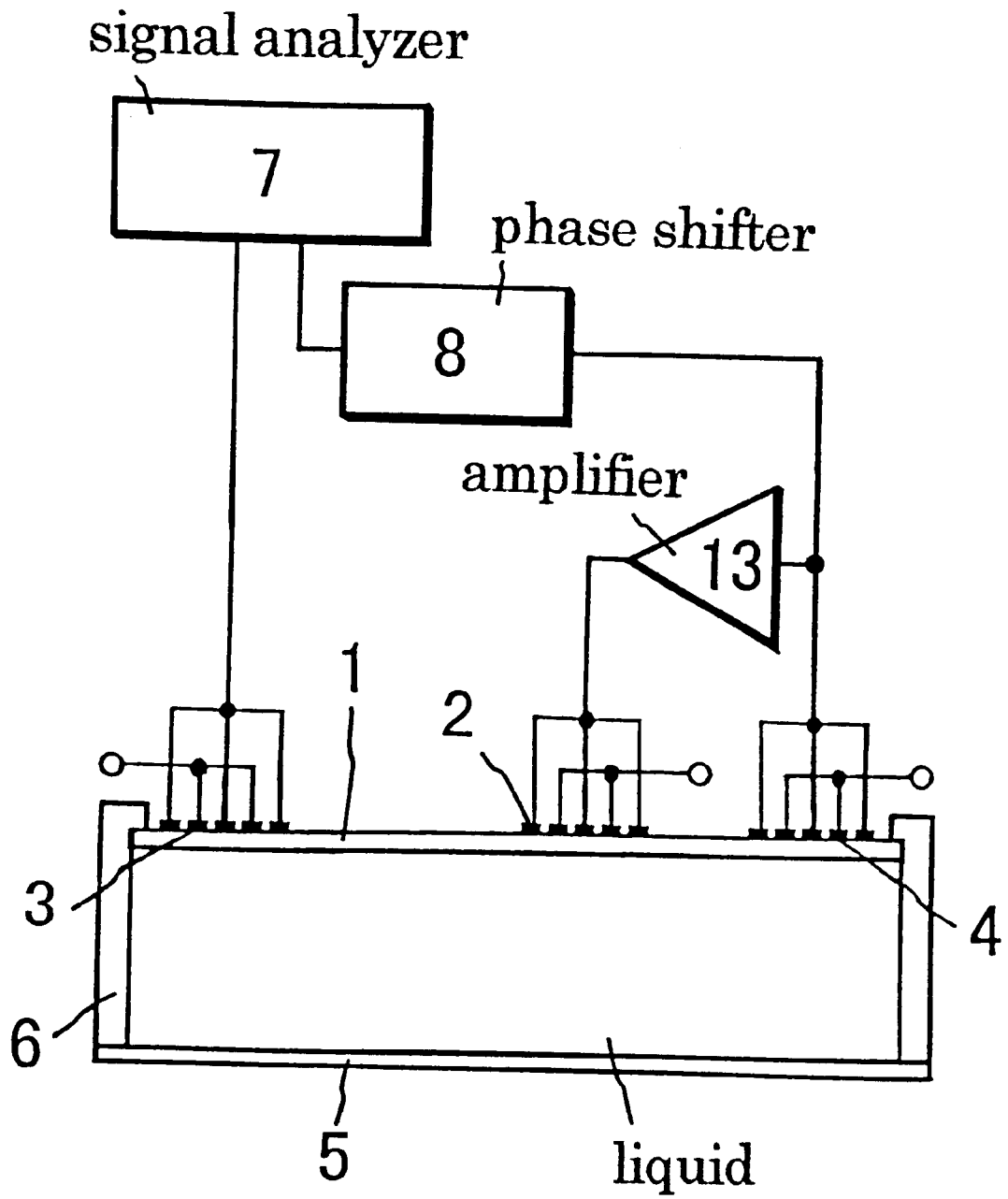
FIG. 7 shows a schematic illustration of a sound pressure sensing device according to a second embodiment of the present invention.

FIG. 7 shows a schematic illustration of a sound pressure sensing device according to a second embodiment of the present invention. The sound pressure sensing device comprises piezoelectric substrate 1, input interdigital transducer 2, first output interdigital transducer 3, second output interdigital transducer 4, diaphragm 5, liquid tank 6, signal analyzer 7, phase shifter 8, and amplifier 13, which is connected between input interdigital transducer 2 and second output interdigital transducer 4.

In the sound pressure sensing device in FIG. 7, if an input electric signal is applied to input interdigital transducer 2, an elastic wave is excited in piezoelectric substrate 1. A leaky component of the elastic wave is radiated effectively in the form of a longitudinal wave into the liquid, and then, reflected by diaphragm 5. A reflected longitudinal wave is detected at first output interdigital transducer 3 as a first delayed electric signal. A non-leaky component of the elastic wave is transmitted to second output interdigital transducer 4, and detected at second output interdigital transducer 4 as a second delayed electric signal. A part of the second delayed electric signal is amplified via amplifier 13, and is fed back as the input electric signal again. Thus, input interdigital transducer 2, second output interdigital transducer 4 and amplifier 13 form a self-oscillation type of delay-line oscillator. A remaining part of the second delayed electric signal is transmitted to signal analyzer 7, where an acoustic phase delay of the first delayed electric signal is compared with that of the second delayed electric signal. In this time, the phase of the first delayed electric signal is controlled to be coincident with that of the second delayed electric signal by phase shifter 8, when sensing no sound pressure. If diaphragm 5 senses a sound pressure, a phase difference between the first- and second delayed electric signals appears at signal analyzer 7. Accordingly, a sound pressure through diaphragm 5 can be sensed by signal analyzer 7 in terms of the phase difference with a high sensitivity.

FIG. 8 shows a schematic illustration of a sound pressure sensing device according to a third embodiment of the present invention. The sound pressure sensing device has the same construction as FIG. 7, except for a position of amplifier 13, which is connected between input interdigital transducer 2 and first output interdigital transducer 3.

In the sound pressure sensing device in FIG. 8, a part of a first delayed electric signal detected at first output interdigital transducer 3 is amplified via amplifier 13, and is fed back as the input electric signal again. Thus, input interdigital transducer 2, first output interdigital transducer 3 and amplifier 13 form a self-oscillation type of delay-line oscillator. A sound pressure through diaphragm 5 can be sensed by signal analyzer 7 in terms of the phase difference between the first- and second delayed electric signals with a high sensitivity.

Figure 9:
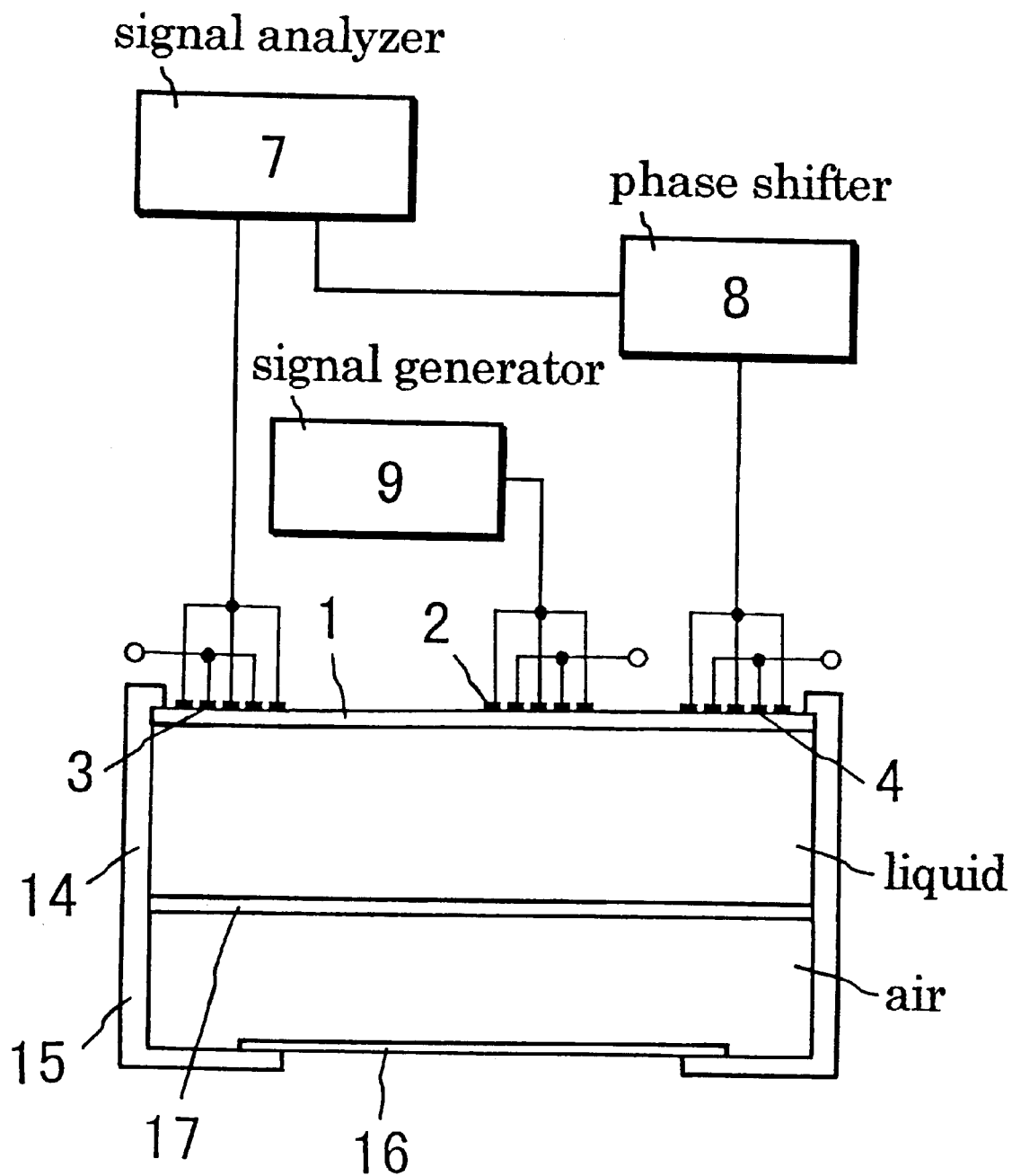
FIG. 9 shows a schematic illustration of a sound pressure sensing device according to a fourth embodiment of the present invention.

FIG. 9 shows a schematic illustration of a sound pressure sensing device according to a fourth embodiment of the present invention. The sound pressure sensing device comprises piezoelectric substrate 1, input interdigital transducer 2, first output interdigital transducer 3, second output interdigital transducer 4, signal analyzer 7, phase shifter 8, signal generator 9, and a tank consisting of liquid room 14, air room 15 with diaphragm panel 16, and partition wall 17 between liquid room 14 and air room 15. Diaphragm panel 16 and partition wall 17 are made of a polymer film and a rubber film, respectively. Input interdigital transducer 2, first output interdigital transducer 3 and second output interdigital transducer 4 are formed on one end surface of piezoelectric substrate 1. A liquid in liquid room 14 is in contact with the other end surface of piezoelectric substrate 1. When sensing, for example, a heartbeat, an outer surface of diaphragm panel 16 is kept in touching with a breast. Thus, the sound pressure sensing device in FIG. 9 has a small size which is very light in weight and has a simple structure.

In the sound pressure sensing device in FIG. 9, when an input electric signal is applied from signal generator 9 to input interdigital transducer 2, an elastic wave is excited in piezoelectric substrate 1, in the same way as FIG. 1. A leaky component of the elastic wave is radiated effectively in the form of a longitudinal wave into the liquid, and then, reflected by partition wall 17. A reflected longitudinal wave is detected at first output interdigital transducer 3 as a first delayed electric signal. A non-leaky component of the elastic wave is detected at second output interdigital transducer 4 as a second delayed electric signal. If diaphragm panel 16 senses a sound pressure, diaphragm panel 16 is mechanically vibrated. As a result, partition wall 17 is also vibrated. Therefore, a length of traveling path of the longitudinal wave is changed. A change in length of traveling path brings about a difference between an acoustic phase delay of the first delayed electric signal and that of the second delayed electric signal. Accordingly, a sound pressure through diaphragm panel 16 can be sensed by signal analyzer 7 in terms of a phase difference with a high sensitivity.

It is possible for the sound pressure sensing device in FIG. 9 to have a construction as FIG. 7 or 8, that is, the construction without signal generator 9 and with amplifier 13.

While this invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

What is claimed is:

1. A sound pressure sensing device comprising:
   a piezoelectric substrate having two end surfaces;
   an input interdigital transducer formed on one end surface of said piezoelectric substrate;
   a first output interdigital transducer having the same interdigital periodicity as said input interdigital transducer and formed on said end surface of said piezoelectric substrate such that said input- and said first output interdigital transducers are located to be symmetrical to a line;

a second output interdigital transducer having the same interdigital periodicity as said input interdigital transducer and the electrode fingers situated along those of said input interdigital transducer, and formed on said end surface of said piezoelectric substrate such that said input interdigital transducer is located between said first- and second output interdigital transducers;

a flat-shaped diaphragm with a flexibility sensitive to a sound pressure, and having an inner- and an outer surfaces, said inner surface being parallel to the other end surface of said piezoelectric substrate;

a liquid tank having a liquid in contact with said other end surface of said piezoelectric substrate and said inner surface of said diaphragm; and a signal analyzer, said piezoelectric substrate, said input interdigital transducer, said first- and second output interdigital transducers forming a sensing assembly, said input interdigital transducer receiving an input electric signal, exciting an elastic wave, composed of a leaky- and a non-leaky components, in said piezoelectric substrate, and radiating said leaky component of said elastic wave in the form of a longitudinal wave into said liquid, said diaphragm reflecting said longitudinal wave, said first output interdigital transducer detecting a reflected longitudinal wave as a first delayed electric signal, said second output interdigital transducer detecting said non-leaky component of said elastic wave as a second delayed electric signal, said signal analyzer sensing a sound pressure caused by touching said outer surface of said diaphragm from a difference between said first- and second delayed electric signals.

2. A sound pressure sensing device as defined in claim 1 further comprising an amplifier connected between said input interdigital transducer and said second output interdigital transducer, said amplifier amplifying said second delayed electric signal, and said input interdigital transducer, said second output interdigital transducer and said amplifier forming a delay-line oscillator.

3. A sound pressure sensing device as defined in claim 1 further comprising an amplifier connected between said input interdigital transducer and said first output interdigital transducer, said amplifier amplifying said first delayed electric signal, and said input interdigital transducer, said first output interdigital transducer and said amplifier forming a delay-line oscillator.

4. A sound pressure sensing device as defined in claim 1, wherein said signal analyzer comprises a phase comparator, which compares an acoustic phase delay of said first delayed electric signal with that of said second delayed electric signal, and senses said sound pressure in terms of a phase difference between said first- and second delayed electric signals.

5. A sound pressure sensing device as defined in claim 1, wherein all said input-, said first output-, and said second output interdigital transducers have an arch-shape, respectively, and are arranged to have one concentric center.

6. A sound pressure sensing device as defined in claim 1, wherein said piezoelectric substrate is made of a piezoelectric ceramic thin plate, the polarization axis thereof being parallel to the thickness direction thereof.

7. A sound pressure sensing device as defined in claim 1, wherein said piezoelectric substrate is made of a piezoelectric polymer thin plate.

8. A sound pressure sensing device as defined in claim 1, wherein said diaphragm is made of a polymer film.

9. A sound pressure sensing device as defined in claim 1, wherein said in diaphragm is made of a metal film.

10. A sound pressure sensing device comprising:

a piezoelectric substrate having two end surfaces;

an input interdigital transducer formed on one end surface of said piezoelectric substrate;

a first output interdigital transducer having the same interdigital periodicity as said input interdigital transducer and formed on said end surface of said piezoelectric substrate such that said input- and said first output interdigital transducers are located to be symmetrical to a line;

a second output interdigital transducer having the same interdigital periodicity as said input interdigital transducer and the electrode fingers situated along those of said input interdigital transducer, and formed on said end surface of said piezoelectric substrate such that said input interdigital transducer is located between said first- and second output interdigital transducers;

a tank having a liquid room with a liquid in contact with the other end surface of said piezoelectric substrate, an air room with a diaphragm panel, which has a flexibility sensitive to a sound pressure and has an inner- and an outer surfaces, and a flat-shaped partition wall with a flexibility sensitive to a sound pressure, and placed between said liquid- and air rooms, and having one surface facing said liquid room and the other surface facing said air room, said one surface facing said liquid room being parallel to said other end surface of said piezoelectric substrate;

a signal analyzer, said piezoelectric substrate, said input interdigital transducer, said first- and second output interdigital transducers forming a sensing assembly, said input interdigital transducer receiving an input electric signal, exciting an elastic wave, composed of a leaky- and a non-leaky components, in said piezoelectric substrate, and radiating said leaky component of said elastic wave in the form of a longitudinal wave into said liquid, said partition wall reflecting said longitudinal wave, said first output interdigital transducer detecting a reflected longitudinal wave as a first delayed electric signal, said second output interdigital transducer detecting said non-leaky component of said elastic wave as a second delayed electric signal, said signal analyzer sensing a sound pressure caused by touching said outer surface of said diaphragm panel from a difference between said first- and second delayed electric signals.

11. A sound pressure sensing device as defined in claim 10 further comprising an amplifier connected between said input interdigital transducer and said second output interdigital transducer, said amplifier amplifying said second delayed electric signal, and said input interdigital transducer, said second output interdigital transducer and said amplifier forming a delay-line oscillator.

12. A sound pressure sensing device as defined in claim 10 further comprising an amplifier connected between said input interdigital transducer and said first output interdigital transducer, said amplifier amplifying said first delayed electric signal, and said input interdigital transducer, said first output interdigital transducer and said amplifier forming a delay-line oscillator.

13. A sound pressure sensing device as defined in claim 10, wherein said signal analyzer comprises a phase comparator, which compares an acoustic phase delay of said first delayed electric signal with that of said second delayed electric signal, and senses said sound pressure in terms of a phase difference between said first- and second delayed electric signals.

14. A sound pressure sensing device as defined in claim 10, wherein all said input-, said first output-, and said second output interdigital transducers have an arch-shape, respectively, and are arranged to have one concentric center.

15. A sound pressure sensing device as defined in claim 10, wherein said piezoelectric substrate is made of a piezoelectric ceramic thin plate, the polarization axis thereof being parallel to the thickness direction thereof.

16. A sound pressure sensing device as defined in claim 10, wherein said piezoelectric substrate is made of a piezoelectric polymer thin plate.

17. A sound pressure sensing device as defined in claim 10, wherein said diaphragm is made of a polymer film.

18. A sound pressure sensing device as defined in claim 10, wherein said diaphragm is made of a metal film.

19. A sound pressure sensing device as defined in claim 10, wherein said partition wall is made of a rubber film.

* * * * *